US011572323B2

(12) United States Patent
De Baerdemaeker et al.

(10) Patent No.: US 11,572,323 B2
(45) Date of Patent: Feb. 7, 2023

(54) CATALYZED PROCESS FOR THE DIMERIZATION OF ALKENES

(71) Applicant: BASF SE, Ludwigshafen am Rhein (DE)

(72) Inventors: Trees Maria De Baerdemaeker, Ludwigshafen am Rhein (DE); Andrei-Nicolae Parvulescu, Ludwigshafen am Rhein (DE); Ivana Jevtovikj, Heidelberg (DE); Craig Jon Cain-Borgman, Iselin, NJ (US); Ulrich Mueller, Ludwigshafen am Rhein (DE); Andreas Kuschel, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 17/427,319

(22) PCT Filed: Jan. 30, 2020

(86) PCT No.: PCT/EP2020/052322
§ 371 (c)(1),
(2) Date: Jul. 30, 2021

(87) PCT Pub. No.: WO2020/157216
PCT Pub. Date: Aug. 6, 2020

(65) Prior Publication Data
US 2022/0127207 A1    Apr. 28, 2022

(30) Foreign Application Priority Data

Jan. 31, 2019   (EP) .................................... 19154774

(51) Int. Cl.
*C07C 2/12*      (2006.01)
*B01J 29/70*     (2006.01)

(52) U.S. Cl.
CPC ............. *C07C 2/12* (2013.01); *B01J 29/7007* (2013.01)

(58) Field of Classification Search
CPC ..................................................... C07C 2/12
See application file for complete search history.

(56) References Cited

U.S. PATENT DOCUMENTS

| 2003/0100811 | A1  | 5/2003 | Dakka et al.      |
| 2004/0181106 | A1  | 9/2004 | Nurminen et al.   |
| 2007/0191662 | A1* | 8/2007 | Oikarinen ................. C07C 2/12 585/533 |
| 2015/0218063 | A1* | 8/2015 | Jana ........................ B01J 29/46 585/510 |

FOREIGN PATENT DOCUMENTS

| EP | 1167326    | A1 | 1/2002  |
| EP | 2698198    | A1 | 2/2014  |
| WO | 95/22516   | A1 | 8/1995  |
| WO | 2006/070073| A1 | 7/2006  |
| WO | 2007/144474| A1 | 12/2007 |
| WO | 2013/064302| A1 | 5/2013  |

OTHER PUBLICATIONS

Wei et al. ("Determination of different acid sites in Beta zeolite for anisole acylation with acetic anhydride", Journal of Catalysis 307 (2013) 103-110). (Year: 2013).*
Wu et al. ("The Synergistic Effect of Acidic Properties and Channel Systems of Zeolites on the Synthesis of Polyoxymethylene Dimethyl Ethers from Dimethoxymethane and Trioxymethylene", ; Published: Aug. 23, 2019). (Year: 2019).*
International Preliminary Report on Patentability received for PCT Patent Application No. PCT/EP2020/052322, dated Aug. 12, 2021, 8 pages.
International Search Report and Written Opinion received for PCT Patent Application No. PCT/EP2020/052322, dated Apr. 2, 2020, 11 pages.

* cited by examiner

*Primary Examiner* — Ali Z Fadhel
(74) *Attorney, Agent, or Firm* — Faegre Drinker Biddle & Reath LLP

(57) ABSTRACT

The present invention relates to a process for the dimerization of alkenes comprising (1) providing a gas stream comprising one or more alkenes; and (2) contacting the gas stream provided in (1) with a catalyst for obtaining a mixture M1 comprising one or more dimerization products of the one or more alkenes, wherein the catalyst in (2) comprises a zeolitic material having a framework structure type selected from the group consisting of MOR, BEA, FER, MFI, TON, FAU, and mixtures of two or more thereof, wherein the framework structure of the zeolitic material comprises $YO_2$, wherein Y stands for one or more tetravalent elements.

14 Claims, No Drawings

CATALYZED PROCESS FOR THE DIMERIZATION OF ALKENES

CROSS-REFERENCE TO RELATED APPLICATIONS

This application is a national stage application (under 35 U.S.C. § 371) of PCT/EP2020/052322, filed Jan. 30, 2020, which claims benefit of European Application No. 19154774.4, filed Jan. 31, 2019, both of which are incorporated herein by reference in their entirety.

TECHNICAL FIELD

The present invention relates to a catalytic process for the dimerization of alkenes using a zeolitic material as the catalyst.

INTRODUCTION

The dimerization of alkenes is an important reaction for the synthesis of higher molecular weight alkenes, and in particular of highly branched products such as 2,4,4-trimethylpentenes, which are the unsaturated precursors of 2,4,4-trimethylpentane (reference compound for 100 "octane" in the assignment of anti-knock ratings in gasoline). In the prior art, the dimerization of alkenes is commonly carried out using acidic resins and selectivity enhancers such as methanol and 2-butanol.

The disadvantages of said prior art process includes:

non-optimized selectivities, in particular with regard to the dimerization of alkenes to highly branched products, and the use of selectivity enhancers.

There is therefore the need for an improved process for the dimerization of alkenes which may achieve higher selectivities towards highly branched products.

DETAILED DESCRIPTION

It was therefore an object of the present invention to provide a process for the dimerization of alkenes which is economically advantageous and can be carried out with high yield and selectivity towards the dimerization products, particularly over extended reaction times. Furthermore, it was an object of the present invention to provide a process for the dimerization of alkenes which displays a high selectivity towards highly branched products. In addition to these it was also an object of the present invention to provide a process for the dimerization of alkenes which employs a catalyst which may be regenerated in a time- and cost-effective manner without suffering notable loss in the catalyst performance even after multiple regeneration cycles. Thus, it has surprisingly been found that a process for the dimerization of alkenes affording a high selectivity towards the dimerization products, and in particular towards highly branched dimerization products, may be provided by using specific zeolitic materials as the catalyst. Furthermore, it has unexpectedly been found that the use of zeolitic materials not only allows for a maintenance of the dimerization reaction with a high alkene conversion rate over extended reaction times, but furthermore that the zeolitic materials may be easily regenerated and provide a performance comparable to the fresh catalyst even after multiple regeneration cycles.

Therefore, the present invention relates to a process for the dimerization of alkenes comprising (1) providing a gas stream comprising one or more alkenes; and (2) contacting the gas stream provided in (1) with a catalyst for obtaining a mixture M1 comprising one or more dimerization products of the one or more alkenes, wherein the catalyst in (2) comprises a zeolitic material having a framework structure type selected from the group consisting of MOR, BEA, FER, MFI, TON, FAU, and mixtures of two or more thereof, wherein the framework structure of the zeolitic material comprises $YO_2$, wherein Y stands for one or more tetravalent elements.

According to the present invention, it is preferred that the zeolitic material has a framework structure type selected from the group consisting of MOR, BEA, MFI, and mixtures of two or three thereof, wherein more preferably the zeolitic material has an MOR and/or a BEA type framework structure, more preferably a BEA type framework structure.

As regards the specific zeolite or the specific zeolites which may be comprised in the zeolitic material used in the inventive process, no particular restrictions apply, provided that the zeolitic material has a framework type selected from the group consisting of MOR, BEA, FER, MFI, TON, FAU, and mixtures of two or more thereof. Thus, by way of example, it is preferred according to the present invention that the zeolitic material comprises one or more zeolites selected from the group consisting of mordenite, zeolite beta, ferrierite, ZSM-5, ZSM-22, and zeolite Y, wherein more preferably the zeolitic material comprises one or more zeolites selected from the group consisting of mordenite, zeolite beta, and ZSM-5, wherein more preferably the zeolitic material comprised in the catalyst comprises mordenite and/or zeolite beta, more preferably zeolite beta, wherein more preferably the zeolitic material comprised in the catalyst is mordenite and/or zeolite beta, more preferably zeolite beta.

No particular restriction applies according to the present invention as to the ions contained at the ion-exchange sites of the zeolitic material, wherein it is preferred that the zeolitic material comprises $H^+$ at the ion-exchange sites of the zeolitic framework, wherein more preferably the zeolitic material is in the H-form.

According to the present invention, it is preferred that the zeolitic material comprised in the catalyst contains 5 wt.-% or less of a metal M calculated as the element and based on 100 wt.-% of $YO_2$ contained in the framework structure of the zeolitic material, preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, more preferably 0.001 wt.-% or less, more preferably 0.0005 wt.-% or less, and more preferably 0.0001 wt.-% or less of a metal M calculated as the element and based on 100 wt.-% of $YO_2$ contained in the framework structure of the zeolitic material, wherein the metal M stands for Na, preferably for Na and K, more preferably for alkali metals, and more preferably for alkali and alkaline earth metals.

In principle, there is no restriction with regard to the elements or compounds which may be contained in the zeolitic material. It is, however, preferred according to the present invention that the zeolitic material comprised in the catalyst contains 5 wt. % or less of phosphorous calculated as the element and based on 100 wt.-% of $YO_2$ contained in the framework structure of the zeolitic material, and more preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, more preferably 0.001 wt.-% or less, more preferably 0.0005 wt.-% or less, and more preferably 0.0001 wt.-% or less of phosphorous calculated as the element and based on 100 wt.-% of $YO_2$ contained in the framework structure of the of the zeolitic material.

As regards the ions which may be contained at the ion-exchange sites of the zeolitic material, it is preferred according to the present invention that the zeolitic material comprises one or more metal cations at the ion-exchange sites of the zeolitic framework, wherein the one or more metal cations are preferably selected from the group consisting of alkaline earth metals and rare earth metals, including mixtures of two or more thereof, preferably from the group consisting of Mg, Ca, Sr, Sc, Y, La, Ce, Pr, Nd, and mixtures of two or more thereof, more preferably from the group consisting of Mg, Ca, La, Ce, and mixtures of two or more thereof, wherein more preferably the zeolitic material comprises Mg and/or La at the ion-exchange sites of the zeolitic framework, wherein more preferably the zeolitic material comprises one or more zeolites selected from the group consisting of Mg-ZSM-5, La-ZSM-5, La-mordenite, and mixtures of two or three thereof, more preferably La-ZSM-5 and/or La-mordenite, wherein more preferably the zeolitic material consists of one or more zeolites selected from the group consisting of Mg-ZSM-5, La-ZSM-5, La-mordenite, and mixtures of two or three thereof, wherein more preferably the zeolitic material is La-ZSM-5 and/or La-mordenite.

According to the present invention, the one or more tetravalent elements comprised in the framework structure of the zeolitic material may be any suitable tetravalent elements, wherein it is preferred that Y is selected from the group consisting of Si, Sn, Ti, Zr, Ge, and mixtures of two or more thereof, more preferably from the group consisting of Si, Sn, Ti, and mixtures of two or more thereof, wherein Y preferably comprises Si or both Si and Sn, wherein more preferably Y comprises Si, wherein more preferably Y is either Si or both Si and Sn, wherein more preferably Y is Si, wherein more preferably the zeolitic material comprises zeolite beta with a framework comprising Si and Sn as tetravalent elements, more preferably zeolite beta with a framework with Si and Sn as the tetravalent elements, wherein more preferably the zeolitic material consists zeolite beta with a framework comprising Si and Sn as tetravalent elements, more preferably zeolite beta with a framework with Si and Sn as the tetravalent elements.

It is further preferred according to the present invention that the framework structure of the zeolitic material further comprises $X_2O_3$, wherein X stands for one or more trivalent elements, and wherein X is selected from the group consisting of Al, B, In, Ga, and mixtures of two or more thereof, wherein X preferably comprises Al, wherein more preferably X is Al.

According to the particular and preferred embodiments of the present invention wherein the framework structure of the zeolitic material further comprises $X_2O_3$, it is preferred that the zeolitic material displays a $YO_2:X_2O_3$ molar ratio in the range of from 2 to 300, more preferably from 6 to 200, more preferably from 8 to 150, more preferably from 10 to 100, more preferably from 15 to 80, more preferably from 20 to 70, more preferably from 40 to 60, and more preferably from 45 to 55.

According to the particular and preferred embodiments of the present invention wherein the framework structure of the zeolitic material further comprises $X_2O_3$, it is preferred that the zeolitic material comprises ZSM-5, wherein more preferably the zeolitic material is ZSM-5.

Preferably, the zeolitic material comprised in the catalyst has a total amount of acid sites in the range of from 0.4 to 4 mmol/g, preferably from 0.5 to 3 mmol/g, more preferably from 0.6 to 2.8 mmol/g, more preferably from 0.8 to 2.6 mmol/g, more preferably from 1 to 2.4 mmol/g, more preferably from 1.2 to 2.2 mmol/g, more preferably from 1.4 to 2 mmol/g, more preferably from 1.6 to 1.9 mmol/g, and more preferably from 1.7 to 1.8 mmol/g, wherein the total amount of acid sites is defined as the total molar amount of desorbed ammonia per mass of the zeolitic material determined according to the temperature programmed desorption of ammonia (NH3-TPD).

As regards the total amount of acid sites in the zeolitic material comprised in the catalyst, it is preferred according to the present invention that the total amount of acid sites is defined as the amount of desorbed ammonia per mass of the zeolitic material determined according to the temperature programmed desorption of ammonia (NH3-TPD) in the temperature range of from 150 to 750° C., preferably of from 180 to 680° C., more preferably of from 190 to 630° C., more preferably of from 200 to 600° C., more preferably of from 205 to 570° C., more preferably of from 210 to 540° C., more preferably of from 215 to 490° C., and more preferably of from 220 to 440° C.

With respect to the acid sites in the zeolitic material comprised in the catalyst, there is no particular restriction as to how many of the acid sites are weak, medium, and/or strong acid sites. It is, however, preferred according the present invention that the zeolitic material comprised in the catalyst has a certain amount of medium acid sites, wherein the amount of medium acid sites is in the range of from 0.4 to 4 mmol/g, preferably from 0.5 to 3 mmol/g, more preferably from 0.6 to 2.8 mmol/g, more preferably from 0.8 to 2.6 mmol/g, more preferably from 1 to 2.4 mmol/g, more preferably from 1.2 to 2.2 mmol/g, more preferably from 1.4 to 2 mmol/g, more preferably from 1.6 to 1.9 mmol/g, and more preferably from 1.7 to 1.8 mmol/g. As regards the amount of medium acid sites contained in the zeolitic material comprised in the catalyst, it is preferred according to the present invention that the amount of medium acid sites is defined as the amount of desorbed ammonia per mass of the zeolitic material determined according to the temperature programmed desorption of ammonia (NH3-TPD) in the temperature range of from 150 to 400° C., preferably of from 180 to 320° C., more preferably of from 190 to 280° C., more preferably of from 200 to 250° C., more preferably of from 205 to 240° C., more preferably of from 210 to 230° C., and more preferably of from 215 to 220° C.

According to the present invention, the amount of strong acid sites in the zeolitic material comprised in the catalyst is also not particularly restricted, wherein it is however preferred that the zeolitic material comprised in the catalyst has less than 1 mmol/g of strong acid sites, more preferably less than 0.5 mmol/g, more preferably less than 0.2 mmol/g, more preferably less than 0.1 mmol/g, more preferably less than 0.05 mmol/g, more preferably less than 0.03 mmol/g, more preferably less than 0.02 mmol/g, more preferably less than 0.01 mmol/g, more preferably less than 0.005 mmol/g, and more preferably less than 0.001 mmol/g. As regards the amount of strong acid sites contained in the zeolitic material comprised in the catalyst, it is preferred according to the present invention that the amount of strong acid sites is defined as the amount of desorbed ammonia per mass of the zeolitic material determined according to the temperature programmed desorption of ammonia (NH3-TPD) in the temperature range of from 300 to 750° C., preferably of from 400 to 720° C., more preferably of from 450 to 690° C., more preferably of from 500 to 670° C., more preferably of from 530 to 650° C., more preferably of from 550 to 630° C., more preferably of from 570 to 610° C., and more preferably of from 590 to 600° C.

The total amount of acid sites as well as the amount of medium acid sites and the amount of strong acid sites as used herein may readily be measured by known methods, preferably by temperature-programmed desorption of ammonia (NH$_3$-TPD), preferably with an automated chemisorption analysis unit having a thermal conductivity detector, preferably by continuous analysis of the desorbed species by an online mass spectrometer, preferably the temperature being measured by a Ni/Cr/Ni thermocouple immediately above the sample in a quartz tube, more preferably wherein the online mass spectrometer monitors the desorption of ammonia by utilizing the molecular weight of ammonia of 16, wherein more preferably the automated chemisorption analysis unit is a Micromeritics AutoChem II 2920, wherein more preferably the online mass spectrometer is a OmniStar QMG200 from Pfeiffer Vacuum. Preferably said measurement comprises 1. a preparation step, 2. a saturation with NH$_3$ step, 3. a step wherein excess ammonia is removed and 4. a NH$_3$-TPD step, more preferably wherein the 4. NH$_3$-TPD step for the total amount of acid sites comprises heating under a He flow to 600° C., preferably at a heating rate of 10 K/min, preferably wherein the temperature of 600° C. is then held for 30 minutes. It is more preferred that for determining the amount of medium acid sites, said 4. NH$_3$-TPD step is carried out at the temperature range of from 250 to 500° C. It is more preferred that for determining the amount of strong acid sites, said 4. NH$_3$-TPD step is carried out in the temperature range above 500° C. According to the present invention it is more preferred that the total amount of acid sites as well as the amount of medium acid sites and the amount of strong acid sites as used herein are determined according to the method described herein in the examples under "determination of the acid sites".

Preferably, the one or more alkenes provided in (1) comprise one or more alkenes according to formula (I)

(I)

wherein R and R' are alkyl groups.

Furthermore, it is preferred according to the inventive process that the one or more dimerization products of the one or more alkenes obtained in (2) comprise one or more alkenes according to formula (II)

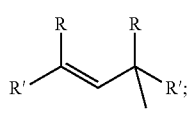

(II)

wherein again R and R' are alkyl groups.

As regards the alkyl groups R and R', it is preferred according to the inventive process that, independently from one another, R and R' are an optionally branched and/or optionally substituted and/or optionally unsaturated alkyl group selected from the group consisting of optionally branched and/or optionally substituted and/or optionally unsaturated C1-C6 alkyl groups, preferably C1-C5 alkyl groups, more preferably C1-C4 alkyl groups, more preferably C1-C3 alkyl groups, more preferably C1-C2 alkyl groups, and more preferably C1 alkyl groups, wherein more preferably R and R' are independently from one another selected from the group consisting of optionally substituted methyl, ethyl, propyl, butyl, pentyl, and hexyl, more preferably from the group consisting of optionally substituted methyl, ethyl, propyl, butyl, and pentyl, more preferably from the group consisting of optionally substituted methyl, ethyl, propyl, and butyl, more preferably from the group consisting of optionally substituted methyl, ethyl, and propyl, wherein more preferably R and R' are independently from one another optionally substituted methyl or ethyl, preferably methyl.

According to the inventive process, it is thus preferred that the one or more alkenes provided in (1) comprise one or more alkenes selected from the group consisting of optionally substituted isobutene, 2-methyl-1-butene, 2-ethyl-1-butene, 2-methyl-1-pentene, 2-ethyl-1-pentene, 2-n-propyl-1-pentene, 2,3-dimethyl-1-butene, 2-ethyl-3-methyl-1-butene, 2-i-propyl-1-pentene, 2-i-propyl-3-methyl-1-butene, and mixtures of two or more thereof, more preferably from the group consisting of optionally substituted isobutene, 2-methyl-1-butene, 2-ethyl-1-butene, 2-methyl-1-pentene, 2-ethyl-1-pentene, 2,3-dimethyl-1-butene, 2-ethyl-3-methyl-1-butene, and mixtures of two or more thereof, more preferably from the group consisting of optionally substituted isobutene, 2-methyl-1-butene, 2-ethyl-1-butene, 2-methyl-1-pentene, 2,3-dimethyl-1-butene, and mixtures of two or more thereof, wherein more preferably the alkene of formula (II) is optionally substituted isobutene and/or 2-methyl-1-butene, preferably isobutene or 2-methyl-1-butene, and more preferably isobutene.

It is preferred according to the inventive process that the one or more dimerization products obtained in (2) comprise one or more alkanes and/or one or more alkenes, preferably one or more alkenes, more preferably one or more C4-C20 alkenes, more preferably one or more C4-C16 alkenes, more preferably one or more C5-C14 alkenes, more preferably one or more C5-C13 alkenes, more preferably one or more C6-C12 alkenes, more preferably one or more C6-C11 alkenes, more preferably one or more C7-C10 alkenes, more preferably one or more C7-C9 alkenes, more preferably one or more C8 alkenes, wherein more preferably the one or more dimerization products obtained in (2) comprise one or more alkenes selected from the group consisting of 1-octene, 2,4,4-trimethyl-1-pentene, 2,4,4-trimethyl-2-pentene, and mixtures of two or three thereof, wherein more preferably the one or more dimerization products obtained in (2) comprise 1-octene and/or 2,4,4-trimethyl-1-pentene, more preferably 2,4,4-trimethyl-1-pentene.

As regards the amount of alkenes contained in the gas stream provided in (1), no particular restrictions apply according to the inventive process, wherein it is preferred that the content of the one or more alkenes in the gas stream provided in (1) and contacted with a catalyst in (2) is in the range of from 5 to 100% by volume based on the total volume of the gas stream, more preferably in the range of from 10 to 99 vol.-%, more preferably in the range of from 15 to 98 vol.-%, more preferably in the range of from 20 to 95 vol.-%, more preferably in the range of from 25 to 90 vol.-%, more preferably in the range of from 30 to 80 vol.-%, more preferably in the range of from 35 to 70 vol.-%, more preferably in the range of from 40 to 60 vol.-%, and more preferably in the range of from 45 to 55 vol.-%.

Although there no particular restrictions apply according to the present invention as to the compounds which may be contained in the gas stream provided in (1), it is preferred that the gas stream provided in (1) and contacted with a catalyst in (2) contains 50 vol.-% or less of aliphatic organic compounds based on the total volume of the gas stream, more preferably 30 vol.-% or less, more preferably 20 vol.-% or less, more preferably 10 vol.-% or less, more preferably 5 vol.-% or less, more preferably 3 vol.-% or less, more preferably 2 vol.-% or less, more preferably 1 vol.-% or less, more preferably 0.5 vol.-% or less, more preferably 0.1 vol.-% or less, more preferably 0.05 vol.-% or less, more preferably 0.01 vol.-% or less, more preferably 0.005 vol.-% or less, and more preferably 0.001 vol.-% or less. According to the present invention, it is preferred that the one or more aliphatic organic compounds are selected from the group consisting of optionally substituted and/or optionally cyclic and and/or optionally branched (C2-C20)hydrocarbons and mixtures of two or more thereof, preferably (C2-C16)hydrocarbons, more preferably (C2-C16)hydrocarbons, more preferably (C2-C14)hydrocarbons, more preferably (C2-C12)hydrocarbons, more preferably (C2-C10)hydrocarbons, more preferably (C2-C8)hydrocarbons, more preferably (C2-C6)hydrocarbons, more preferably (C3-C5)hydrocarbons, and more preferably C4-hydrocarbons and mixtures thereof. As regards the optionally substituted and/or optionally branched hydrocarbons, it is preferred that the one or more optionally substituted and/or optionally cyclic hydrocarbons are branched, wherein more preferably the one or more branched hydrocarbons have the formula

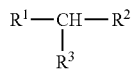

wherein independently from one another $R^1$, $R^2$, and $R^3$ are optionally substituted and/or optionally cyclic and/or optionally branched (C1-C8)alkyl, preferably (C1-C6)alkyl, more preferably (C1-C5)alkyl, wherein more preferably $R^1$, $R^2$, and $R^3$ are, independently from one another, optionally substituted and/or optionally branched (C1-C4)alkyl, preferably (C1-C3)alkyl, wherein more preferably $R^1$, $R^2$, and $R^3$ are, independently from one another, optionally substituted methyl or ethyl, preferably optionally substituted methyl.

Concerning the optional substitution of the one or more aliphatic organic compounds, it is preferred that the one or more aliphatic organic compounds are substituted with one or more functional groups, wherein the one or more functional groups are preferably selected from the group consisting of hydroxyl, halogen, carbonyl, aldehyde, carbonate ester, carboxylate, carboxyl, ester, ether, carboxamide, amine, imine, cyanate, isocyanate, nitrate, nitrile, isonitrile, sulfide, sulfinyl, sulfonyl, sulfino, sulfo, thiocyanate, isothiocyanate, phosphino, phosphono, and phosphate, more preferably from the group consisting of hydroxyl, halogen, carbonyl, aldehyde, carboxylate, carboxyl, ester, ether, carboxamide, amine, imine, cyanate, isocyanate, nitrate, nitrile, isonitrile, and combinations of two or more thereof, more preferably from the group consisting of hydroxyl, halogen, carbonyl, aldehyde, carboxylate, carboxyl, ester, ether, and combinations of two or more thereof, more preferably from the group consisting of hydroxyl, halogen, carbonyl, alkoxy, and combinations of two or more thereof, more preferably from the group consisting of hydroxyl, fluoro, chloro, bromo, (C1-C3)alkoxy, and combinations of two or more thereof, more preferably from the group consisting of hydroxyl, fluoro, chloro, (C1-C2)alkoxy, and combinations of two or more thereof, more preferably from the group consisting of hydroxyl, fluoro, chloro, methoxy, and combinations of two or more thereof, wherein more preferably the one or more aliphatic compounds are substituted with one or more hydroxyl groups.

According to the present invention, it is however alternatively preferred that the one or more aliphatic organic compounds are unsubstituted hydrocarbons, wherein more preferably the one or more aliphatic organic compounds comprise isobutane, wherein more preferably the one or more aliphatic organic compounds are isobutane.

It is, however, preferred that the gas stream provided in (1) and contacted with a catalyst in (2) further comprises one or more inert gases, wherein the one or more inert gases selected from the group consisting of nitrogen, helium, argon, $CO_2$, and mixtures of two or more thereof, preferably from the group consisting of nitrogen, argon, $CO_2$, and mixtures of two or more thereof, wherein more preferably the gas stream further comprises nitrogen and/or argon, more preferably nitrogen and argon. As regards their content, it is preferred that the content of the one or more inert gases in the gas stream provided in (1) and contacted with a catalyst in (2) is in the range of from 0 to 95% by volume based on the total volume of the gas stream, preferably in the range of from 1 to 90 vol.-%, more preferably in the range of from 2 to 85 vol.-%, more preferably in the range of from 5 to 80 vol.-%, more preferably in the range of from 10 to 75 vol.-%, more preferably in the range of from 20 to 70 vol.-%, more preferably in the range of from 30 to 65 vol.-%, more preferably in the range of from 40 to 60 vol.-%, and more preferably in the range of from 45 to 55 vol.-%.

According to the inventive process, it is preferred that contacting in (2) is conducted at a temperature in the range of from 80 to 350° C., more preferably of from 100 to 320° C., more preferably of from 120 to 300° C., more preferably of from 140 to 280° C., more preferably of from 160 to 260° C., more preferably of from 180 to 250° C., more preferably of from 200 to 245° C., more preferably of from 220 to 240° C., and more preferably of from 225 to 235° C.

Furthermore and independently thereof it is preferred that contacting in (2) is conducted at a pressure in the range of from 2 to 80 bar, preferably of from 4 to 60 bar, more preferably of from 6 to 50 bar, more preferably of from 8 to 45 bar, more preferably of from 10 to 40 bar, more preferably of from 12 to 38 bar, more preferably of from 14 to 36 bar, more preferably of from 16 to 34 bar, more preferably of from 18 to 32 bar, more preferably of from 20 to 30 bar, more preferably of from 22 to 28 bar, and more preferably of from 24 to 26 bar.

In principle, the inventive process may be conducted in a continuous mode and/or in a batch mode, such that preferably, contacting in (2) is conducted in a continuous mode and/or in a batch mode, and preferably in a continuous mode.

As concerns the particular and preferred embodiments of the inventive process which are conducted in a continuous mode, it is preferred that the space velocity in the contacting in (2) is in the range of from 10 to 10,000 $h^{-1}$, preferably of from 50 to 5,000 $h^{-1}$, more preferably of from 100 to 3,000 $h^{-1}$, more preferably of from 300 to 2,500 $h^{-1}$, more preferably of from 500 to 1,800 h$^{-1}$, more preferably of from 700 to 1,500 h$^{-1}$, more preferably of from 800 to 1,200 h$^{-1}$, more preferably of from 900 to 1,100 h$^{-1}$. Furthermore and independently thereof, it is preferred that when contacting in (2) is conducted in a continuous mode, the service life of the catalyst during which the continuous process is performed without interruption of the dimerization reaction is in the range of from 50 to 2,000 h, preferably of from 100 to 1,000 h, more preferably of from 150 to 500 h, more preferably of from 200 to 400 h, more preferably of from 230 to 350 h, and more preferably of from 250 to 300 h.

It is preferred that the inventive process further comprises:

(3) separating the unreacted one or more alkenes from the reacted mixture M1 obtained in (2) for obtaining a mixture M2 containing one or more alkenes; and (4) recycling the mixture M2 containing the one or more alkenes to (1).

Furthermore and independently thereof, it is preferred according to the inventive process that the catalyst is regenerated at regular intervals. As regards the regeneration of the catalyst, it is preferred that regeneration is performed by contacting the catalyst with a gas stream containing oxygen, wherein contacting is performed at a temperature in the range of from 250 to 1,000° C., preferably of from 300 to 900° C., more preferably of from 350 to 800° C., more preferably of from 400 to 700° C., more preferably of from 450 to 650° C., and more preferably of from 500 to 600° C. Furthermore and independently thereof, it is preferred that the gas stream for regeneration contains oxygen in an amount of from 0.1 to 25% by volume based on the total volume of the gas stream, preferably of from 0.5 to 20 vol.-%, more preferably of from 1 to 15 vol.-%, more preferably of from 1.5 to 12 vol.-%, more preferably of from 2 to 10 vol.-%, more preferably of from 2.5 to 8 vol.-%, more preferably of from 3 to 7 vol.-%, more preferably of from 3.5 to 6 vol.-%, and more preferably of from 4 to 5 vol.-%. As regards the gas stream for regeneration, it is preferred that it further comprises one or more inert gases, wherein the one or more inert gases selected from the group consisting of nitrogen, helium, argon, CO$_2$, and mixtures of two or more thereof, preferably from the group consisting of nitrogen, argon, CO$_2$, and mixtures of two or more thereof, wherein more preferably the gas stream further comprises nitrogen and/or argon, more preferably nitrogen and argon. With respect to the content of the one or more inert gases in the gas stream for regeneration, it is preferred according to the inventive process that the content is in the range of from 75 to 99.9% by volume based on the total volume of the gas stream, preferably in the range of from 80 to 99.5 vol.-%, more preferably in the range of from 85 to 99 vol.-%, more preferably in the range of from 88 to 98.5 vol.-%, more preferably in the range of from 90 to 98 vol.-%, more preferably in the range of from 92 to 97.5 vol.-%, more preferably in the range of from 93 to 97 vol.-%, more preferably in the range of from 94 to 96.5 vol.-%, and more preferably in the range of from 95 to 96 vol.-%.

As regards the zeolitic material comprised in the catalyst, it is preferred according to the inventive process that in instances wherein the zeolitic material comprised in the catalyst has a framework structure type BEA, the zeolitic material displays an X-ray diffraction pattern comprising at least the following reflections:

| Intensity (%) | Diffraction angle 2θ/° [Cu K(alpha 1)] |
|---|---|
| [12-32] | [21.79-21.99] |
| 100 | [22.28-22.48] |
| [8-28] | [25.18-25.38] |
| [19-39] | [25.71-25.91] |
| [6-26] | [26.96-27.16] |
| [5-25] | [28.62-28.82] |
| [5-25] | [29.43-29.63] |
| [4-24] | [30.23-30.43] |
| [4-24] | [33.06-33.47] |
| [4-24] | [43.21-43.61] | wherein 100% relates to the intensity of the maximum peak in the 20-45° 2θ range of the X-ray powder diffraction pattern, and wherein the BEA-type framework structure comprises YO$_2$ and X$_2$O$_3$, wherein Y is a tetravalent element, and X is a trivalent element. According to said particular and preferred embodiments, it is preferred that the zeolitic material having a BEA-type framework structure displays a YO$_2$:X$_2$O$_3$ molar ratio in the range of from 2 to 100, preferably from 3 to 50, more preferably from 4 to 30, more preferably from 5 to 25, more preferably from 6 to 20, more preferably from 7 to 18, more preferably from 8 to 16, and more preferably from 9 to 14. Furthermore and independently thereof, it is preferred that the zeolitic material comprises zeolite beta, wherein preferably the zeolitic material is zeolite beta. Furthermore and independently thereof it is preferred that the zeolitic material having a BEA-type framework structure comprised in the catalyst is obtainable and/or obtained according to an organotemplate-free synthetic process.

According to the present invention, the term "organotemplate" and "organic structure directing agent" are used synonymously, wherein the term "organotemplate" or "organic structure directing agent" refers to any organic compound, and preferably to any organic compound containing an organocation, which may be added to a synthetic process for the preparation of a zeolitic material having a BEA framework structure as structure directing agent. Furthermore, the term "organotemplate-free" as used in the present application refers to a synthetic process which does not employ an organotemplate as structure directing agent, i.e. which is organotemplate-free, wherein said terms define synthetic processes for the preparation of a zeolitic material having a BEA framework structure wherein at no point in the process does the reaction mixture contain more than 1 wt.-% of an organic structure directing agent based on 100 wt.-% of YO$_2$ contained in the reaction mixture, preferably more than 0.5 wt.-%, more preferably more than 0.1 wt.-%, more preferably more than 0.05 wt.-%, more preferably more than 0.01 wt.-%, more preferably more than 0.005 wt.-% or less, more preferably more than 0.001 wt.-%, more preferably more than 0.0005 wt.-% or less, and more preferably more than 0.0001 wt.-% of an organic structure directing agent based on 100 wt.-% of YO$_2$ contained in the reaction mixture.

With regard to the zeolitic material having a BEA-type framework structure used in the inventive process, no particular restrictions apply relative to the method according to which the X-ray diffraction is obtained for determining the diffraction angles and intensities of the reflections, provided that the Cu K(alpha 1) radiation is used to this effect. According to the inventive process it is however preferred that the X-ray diffraction pattern is obtained from X-ray diffraction experiments on the powdered materials performed using D8 Advance X-ray Diffractometer (Bruker AXS) equipped with a Lynx Eye detector using the Cu K alpha-1 radiation, wherein Cu—Ka radiation is used in a Bragg-Brentano geometry and the data is collected from 2-50° (2θ) using a 0.02° step size and a dwell time of 2.4 seconds per step. Furthermore, it is preferred that the parameters used in the X-ray diffraction experiment are as follows:
Primary side: Divergence Slit, 0.1° with ASS
Secondary side: 0.1 fixed slit
Detector: Lynx Eye, 3°

As regards the preferred organotemplate-free synthetic process according to which the zeolitic material having a BEA-type framework structure is obtained, it is preferred according to the present invention that the organotemplate-free synthetic process comprises (A) preparing a mixture comprising one or more sources for $YO_2$, one or more sources for $X_2O_3$, and seed crystals, the seed crystals comprising a material having a BEA-type framework structure;

(B) crystallizing the mixture obtained in (A) for obtaining a zeolitic material having a BEA-type framework structure; wherein Y is a tetravalent element, and X is a trivalent element, and wherein the mixture prepared in (A) and crystallized in (B) does not contain an organotemplate as structure-directing agent.

Preferably, the mixture prepared in (A) and crystallized in (B) contains 5 wt.-% or less of carbon calculated as the element and based on 100 wt.-% of Y contained in the mixture, preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, more preferably 0.001 wt.-% or less, more preferably 0.0005 wt.-% or less, and more preferably 0.0001 wt.-% or less of carbon calculated as the element and based on 100 wt.-% of Y contained in the mixture.

With respect to the zeolitic material having a BEA-type framework structure obtained in (B), it is preferred that said zeolitic material comprises one or more alkali metals AM, wherein AM is preferably selected from the group consisting of Li, Na, K, Cs, and combinations of two or more thereof, more preferably from the group consisting of Li, Na, K, and combinations of two or more thereof, wherein more preferably the alkali metal AM is Na and/or K, more preferably Na. Furthermore, it is preferred that the molar ratio $AM:YO_2$ in the mixture prepared in (A) and crystallized in (B) is in the range of from 0.05 to 5, preferably from 0.1 to 2, more preferably from 0.3 to 1, more preferably from 0.4 to 0.8, more preferably from 0.45 to 0.7, more preferably from 0.5 to 0.65, and more preferably from 0.55 to 0.6.

As regards the preferred organotemplate-free synthetic process according to which the zeolitic material having a BEA-type framework structure is obtained, it is preferred that Y is selected from the group consisting of Si, Sn, Ti, Zr, Ge, and a mixture of two or more thereof, Y preferably being Si. Furthermore, it is preferred that the one or more sources for $YO_2$ contained in the mixture prepared in (A) and crystallized in (B) comprises one or more silicates, preferably one or more alkali metal silicates, wherein the alkali metal is preferably selected from the group consisting of Li, Na, K, Rb, and Cs, wherein more preferably the alkali metal is Na and/or K, and wherein more preferably the alkali metal is Na, wherein more preferably the one or more sources for $YO_2$ contained in the mixture prepared in (A) and crystallized in (B) comprises water glass, preferably sodium and/or potassium silicate, more preferably sodium silicate. Furthermore, it is preferred that the one or more sources for $YO_2$ contained in the mixture prepared in (A) and crystallized in (B) further comprises one or more silicas, preferably one or more silica hydrosols and/or one or more colloidal silicas, and more preferably one or more colloidal silicas.

With regard to the preferred organotemplate-free synthetic process according to which the zeolitic material having a BEA-type framework structure is obtained, it is preferred that X is selected from the group consisting of Al, B, In, Ga, and a mixture of two or more thereof, X preferably being Al. According to said particular and preferred embodiments, it is preferred that the one or more sources for $X_2O_3$ contained in the mixture prepared in (A) and crystallized in (B) comprises one or more aluminate salts, preferably an aluminate of an alkali metal, wherein the alkali metal is preferably selected from the group consisting of Li, Na, K, Rb, and Cs, wherein more preferably the alkali metal is Na and/or K, and wherein more preferably the alkali metal is Na. Furthermore and independently thereof, it is preferred that the molar ratio $YO_2:X_2O_3$ of the mixture prepared in (A) and crystallized in (B) is in the range of from 1 to 200, preferably from 5 to 100, more preferably from 10 to 50, more preferably from 15 to 40, more preferably from 20 to 30, more preferably from 23 to 25, and more preferably from 23.5 to 24.

As regards the preferred organotemplate-free synthetic process according to which the zeolitic material having a BEA-type framework structure is obtained, it is further preferred that the amount of seed crystals comprised in the mixture prepared in (A) and crystallized in (B) is in the range of from 0.5 to 30 wt.-% based on 100 wt.-% of the one or more sources of $YO_2$ in the mixture, calculated as $YO_2$, preferably from 1 to 25 wt.-%, more preferably from 3 to 20 wt.-%, more preferably from 5 to 15 wt.-%, more preferably from 8 to 12 wt.-%, and more preferably from 9 to 11 wt.-%. Furthermore and independently thereof, it is preferred that the mixture prepared in (A) and crystallized in (B) further comprises one or more solvents, wherein said one or more solvents preferably comprises water, more preferably deionized water, wherein more preferably water is employed as the solvent further comprised in the mixture prepared in (A) and crystallized in (B), preferably deionized water. With respect to the particular and preferred embodiments wherein the one or more solvents comprises water, it is preferred that the molar ratio $H_2O:YO_2$ of the mixture prepared in (A) and crystallized in (B) is in the range of from 5 to 100, preferably from 10 to 50, more preferably from 13 to 30, more preferably from 15 to 20, and more preferably from 17 to 18.

Concerning the preferred organotemplate-free synthetic process according to which the zeolitic material having a BEA-type framework structure is obtained, it is further preferred that the crystallization in (B) involves heating of the mixture, preferably at a temperature in the range of from 80 to 200° C., more preferably from 90 to 180° C., more preferably from 100 to 160° C., more preferably from 110 to 140° C., and more preferably from 115 to 130° C. According to said particular and preferred embodiments, it is preferred that the crystallization in (B) is conducted under autogenous pressure, preferably under solvothermal conditions, and more preferably under hydrothermal conditions.

With respect to the preferred organotemplate-free synthetic process according to which the zeolitic material having a BEA-type framework structure is obtained, it is preferred that in (B) the mixture is heated for a period in the range of from 5 to 200 h, preferably from 20 to 150 h, more preferably from 50 to 100 h, and more preferably from 65 to 75 h.

It is preferred that the organotemplate-free synthetic process according to which the zeolitic material having a BEA-type framework structure is obtained further comprises (C) isolating the zeolitic material having a BEA-type framework structure obtained in (B), preferably by filtration; and (D) optionally washing the zeolitic material having a BEA-type framework structure obtained in (B) or (C), preferably in (C); and/or, (E) optionally drying the zeolitic material having a BEA-type framework structure obtained in (B), (C) or (D), preferably in (D);

wherein the steps (C) and/or (D) and/or (E) can be conducted in any order, and wherein one or more of said steps is preferably repeated one or more times.

Independently thereof, it is preferred that the organotemplate-free synthetic process according to which the zeolitic material having a BEA-type framework structure is obtained further comprises (F) exchanging one or more of the ionic non-framework elements contained in the zeolitic material having a BEA-type framework structure obtained in (C), (D), or (E), preferably in (E), against $H^+$ and/or $NH_4^+$, preferably against $NH_4^+$; and/or, preferably and (G) drying and/or calcining, preferably drying and calcining the zeolitic material having a BEA-type framework structure obtained in (C), (D), (E), or (F).

The present invention is further illustrated by the following set of embodiments and combinations of embodiments resulting from the dependencies and back-references as indicated. In particular, it is noted that in each instance where a range of embodiments is mentioned, for example in the context of a term such as "The process of any one of embodiments 1 to 4", every embodiment in this range is meant to be explicitly disclosed for the skilled person, i.e. the wording of this term is to be understood by the skilled person as being synonymous to "The process of any one of embodiments 1, 2, 3, and 4".

1. A process for the dimerization of alkenes comprising
   (1) providing a gas stream comprising one or more alkenes; and
   (2) contacting the gas stream provided in (1) with a catalyst for obtaining a mixture M1 comprising one or more dimerization products of the one or more alkenes, wherein the catalyst in (2) comprises a zeolitic material having a framework structure type selected from the group consisting of MOR, BEA, FER, MFI, TON, FAU, and mixtures of two or more thereof,
   wherein the framework structure of the zeolitic material comprises $YO_2$, wherein Y stands for one or more tetravalent elements.

2. The process of embodiment 1, wherein the zeolitic material has a framework structure type selected from the group consisting of MOR, BEA, MFI, and mixtures of two or three thereof, wherein preferably the zeolitic material has an MOR and/or a BEA type framework structure, more preferably a BEA type framework structure.

3. The process of embodiment 1 or 2, wherein the zeolitic material comprises one or more zeolites selected from the group consisting of mordenite, zeolite beta, ferrierite, ZSM-5, ZSM-22, and zeolite Y, preferably from the group consisting of mordenite, zeolite beta, and ZSM-5, wherein more preferably the zeolitic material comprised in the catalyst comprises mordenite and/or zeolite beta, more preferably zeolite beta, wherein more preferably the zeolitic material comprised in the catalyst is mordenite and/or zeolite beta, more preferably zeolite beta.

4. The process of any of embodiments 1 to 3, wherein the zeolitic material comprises $H^+$ at the ion-exchange sites of the zeolitic framework, wherein preferably the zeolitic material is in the H-form.

5. The process of any of embodiments 1 to 4, wherein the zeolitic material comprised in the catalyst contains 5 wt.-% or less of a metal M calculated as the element and based on 100 wt.-% of $YO_2$ contained in the framework structure of the zeolitic material, preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, more preferably 0.001 wt.-% or less, more preferably 0.0005 wt.-% or less, and more preferably 0.0001 wt.-% or less of a metal M calculated as the element and based on 100 wt.-% of $YO_2$ contained in the framework structure of the zeolitic material, wherein the metal M stands for Na, preferably for Na and K, more preferably for alkali metals, and more preferably for alkali and alkaline earth metals.

6. The process of any of embodiments 1 to 5, wherein the zeolitic material comprised in the catalyst contains 5 wt.% or less of phosphorous calculated as the element and based on 100 wt.-% of $YO_2$ contained in the framework structure of the zeolitic material, preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, more preferably 0.001 wt.-% or less, more preferably 0.0005 wt.-% or less, and more preferably 0.0001 wt.-% or less of phosphorous calculated as the element and based on 100 wt.-% of $YO_2$ contained in the framework structure of the of the zeolitic material.

7. The process of any of embodiments 1 to 6, wherein the zeolitic material comprises one or more metal cations at the ion-exchange sites of the zeolitic framework, wherein the one or more metal cations are selected from the group consisting of alkaline earth metals and rare earth metals, including mixtures of two or more thereof, preferably from the group consisting of Mg, Ca, Sr, Sc, Y, La, Ce, Pr, Nd, and mixtures of two or more thereof, more preferably from the group consisting of Mg, Ca, La, Ce, and mixtures of two or more thereof, wherein more preferably the zeolitic material comprises Mg and/or La at the ion-exchange sites of the zeolitic framework, wherein more preferably the zeolitic material comprises one or more zeolites selected from the group consisting of Mg-ZSM-5, La-ZSM-5, La-mordenite, and mixtures of two or three thereof, more preferably La-ZSM-5 and/or La-mordenite, wherein more preferably the zeolitic material consists of one or more zeolites selected from the group consisting of Mg-ZSM-5, La-ZSM-5, La-mordenite, and mixtures of two or three thereof, wherein more preferably the zeolitic material is La-ZSM-5 and/or La-mordenite.

8. The process of any of embodiments 1 to 7, wherein Y is selected from the group consisting of Si, Sn, Ti, Zr, Ge, and mixtures of two or more thereof, preferably from the group consisting of Si, Sn, Ti, and mixtures of two or more thereof, wherein Y preferably comprises Si or both Si and Sn, wherein more preferably Y comprises Si, wherein more preferably Y is either Si or both Si and Sn, wherein more preferably Y is Si, wherein more preferably the zeolitic material comprises zeolite beta with a framework comprising Si and Sn as tetravalent elements, more preferably zeolite beta with a framework with Si and Sn as the tetravalent elements, wherein more preferably the zeolitic material consists zeolite beta with a framework comprising Si and Sn as tetravalent elements, more preferably zeolite beta with a framework with Si and Sn as the tetravalent elements.

9. The process of any of embodiments 1 to 8, wherein framework structure of the zeolitic material further comprises $X_2O_3$, wherein X stands for one or more trivalent elements, and wherein X is selected from the group consisting of Al, B, In, Ga, and mixtures of two or more thereof, wherein X preferably comprises Al, wherein more preferably X is Al.

10. The process of embodiment 9, wherein the zeolitic material displays a $YO_2:X_2O_3$ molar ratio in the range of from 2 to 300, preferably from 6 to 200, more preferably from 8 to 150, more preferably from 10 to 100, more preferably from 15 to 80, more preferably from 20 to 70, more preferably from 40 to 60, and more preferably from 45 to 55.

11. The process of embodiment 9 or 10, wherein the zeolitic material comprises ZSM-5, wherein preferably the zeolitic material is ZSM-5.

12. The process of any of embodiments 1 to 11, wherein the zeolitic material comprised in the catalyst has a total amount of acid sites in the range of from 0.4 to 4 mmol/g, preferably from 0.5 to 3 mmol/g, more preferably from 0.6 to 2.8 mmol/g, more preferably from 0.8 to 2.6 mmol/g, more preferably from 1 to 2.4 mmol/g, more preferably from 1.2 to 2.2 mmol/g, more preferably from 1.4 to 2 mmol/g, more preferably from 1.6 to 1.9 mmol/g, and more preferably from 1.7 to 1.8 mmol/g,
wherein the total amount of acid sites is defined as the total molar amount of desorbed ammonia per mass of the zeolitic material determined according to the temperature programmed desorption of ammonia (NH3-TPD).

13. The process of embodiment 12, wherein the total amount of acid sites is defined as the amount of desorbed ammonia per mass of the zeolitic material determined according to the temperature programmed desorption of ammonia (NH3-TPD) in the temperature range of from 150 to 750° C., preferably of from 180 to 680° C., more preferably of from 190 to 630° C., more preferably of from 200 to 600° C., more preferably of from 205 to 570° C., more preferably of from 210 to 540° C., more preferably of from 215 to 490° C., and more preferably of from 220 to 440° C.

14. The process of any of embodiments 1 to 13, wherein the zeolitic material comprised in the catalyst has an amount of medium acid sites, wherein the amount of medium acid sites is in the range of from 0.4 to 4 mmol/g, preferably from 0.5 to 3 mmol/g, more preferably from 0.6 to 2.8 mmol/g, more preferably from 0.8 to 2.6 mmol/g, more preferably from 1 to 2.4 mmol/g, more preferably from 1.2 to 2.2 mmol/g, more preferably from 1.4 to 2 mmol/g, more preferably from 1.6 to 1.9 mmol/g, and more preferably from 1.7 to 1.8 mmol/g.

15. The process of embodiment 14, wherein the amount of medium acid sites is defined as the amount of desorbed ammonia per mass of the zeolitic material determined according to the temperature programmed desorption of ammonia (NH3-TPD) in the temperature range of from 150 to 400° C., preferably of from 180 to 320° C., more preferably of from 190 to 280° C., more preferably of from 200 to 250° C., more preferably of from 205 to 240° C., more preferably of from 210 to 230° C., and more preferably of from 215 to 220° C.

16. The process of any of embodiments 1 to 15, wherein the zeolitic material comprised in the catalyst has less than 1 mmol/g of strong acid sites, preferably less than 0.5 mmol/g, more preferably less than 0.2 mmol/g, more preferably less than 0.1 mmol/g, more preferably less than 0.05 mmol/g, more preferably less than 0.03 mmol/g, more preferably less than 0.02 mmol/g, more preferably less than 0.01 mmol/g, more preferably less than 0.005 mmol/g, and more preferably less than 0.001 mmol/g.

17. The process of embodiment 16, wherein the amount of strong acid sites is defined as the amount of desorbed ammonia per mass of the zeolitic material determined according to the temperature programmed desorption of ammonia (NH3-TPD) in the temperature range of from 300 to 750° C., preferably of from 400 to 720° C., more preferably of from 450 to 690° C., more preferably of from 500 to 670° C., more preferably of from 530 to 650° C., more preferably of from 550 to 630° C., more preferably of from 570 to 610° C., and more preferably of from 590 to 600° C.

18. The process of any of embodiments 1 to 17, wherein the one or more alkenes provided in (1) comprise one or more alkenes according to formula (I)

wherein R and R' are alkyl groups.

19. The process of any of embodiments 1 to 18, wherein the one or more dimerization products of the one or more alkenes obtained in (2) comprise one or more alkenes according to formula (II)

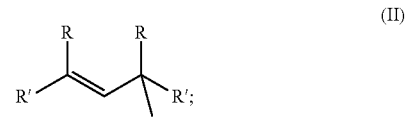

wherein R and R' are alkyl groups.

20. The process of embodiments 18 or 19, wherein independently from one another, R and R' are an optionally branched and/or optionally substituted and/or optionally unsaturated alkyl group selected from the group consisting of optionally branched and/or optionally substituted and/or optionally unsaturated C1-C6 alkyl groups, preferably C1-C5 alkyl groups, more preferably C1-C4 alkyl groups, more preferably C1-C3 alkyl groups, more preferably C1-C2 alkyl groups, and more preferably C1 alkyl groups, wherein more preferably R and R' are independently from one another selected from the group consisting of optionally substituted methyl, ethyl, propyl, butyl, pentyl, and hexyl, more preferably from the group consisting of optionally substituted methyl, ethyl, propyl, butyl, and pentyl, more preferably from the group consisting of optionally substituted methyl, ethyl, propyl, and butyl, more preferably from the group consisting of optionally substituted methyl, ethyl, and propyl, wherein more preferably R and R' are independently from one another optionally substituted methyl or ethyl, preferably methyl.

21. The process of any of embodiments 1 to 20, wherein the one or more alkenes provided in (1) comprise one or more alkenes selected from the group consisting of optionally substituted isobutene, 2-methyl-1-butene, 2-ethyl-1-butene, 2-methyl-1-pentene, 2-ethyl-1-pentene, 2-n-propyl-1-pentene, 2,3-dimethyl-1-butene, 2-ethyl-3-methyl-1-butene, 2-i-propyl-1-pentene, 2-i-propyl-3-methyl-1-butene, and mixtures of two or more thereof, more preferably from the group consisting of optionally substituted isobutene, 2-methyl-1-butene, 2-ethyl-1-butene, 2-methyl-1-pentene, 2-ethyl-1-pentene, 2,3-dimethyl-1-butene, 2-ethyl-3-methyl-1-butene, and mixtures of two or more thereof, more preferably from the group consisting of optionally substituted isobutene, 2-methyl-1-butene, 2-ethyl-1-butene, 2-methyl-1-pentene, 2,3-dimethyl-1-butene, and mixtures of two or more thereof, wherein more preferably the alkene of formula (II) is optionally substituted isobutene and/or 2-methyl-1-butene, preferably isobutene or 2-methyl-1-butene, and more preferably isobutene.

22. The process of any of embodiments 1 to 21, wherein the one or more dimerization products obtained in (2) comprise one or more alkanes and/or one or more alkenes, preferably one or more alkenes, more preferably one or more C4-C20 alkenes, more preferably one or more C4-C16 alkenes, more preferably one or more C5-C14 alkenes, more preferably one or more C5-C13 alkenes, more preferably one or more C6-C12 alkenes, more preferably one or more C6-C11 alkenes, more preferably one or more C7-C10 alkenes, more preferably one or more C7-C9 alkenes, more preferably one or more C8 alkenes, wherein more preferably the one or more dimerization products obtained in (2) comprise one or more alkenes selected from the group consisting of 1-octene, 2,4,4-trimethyl-1-pentene, 2,4,4-trimethyl-2-pentene, and mixtures of two or three thereof, wherein more preferably the one or more dimerization products obtained in (2) comprise 1-octene and/or 2,4,4-trimethyl-1-pentene, more preferably 2,4,4-trimethyl-1-pentene.

23. The process of any of embodiments 1 to 22, wherein the content of the one or more alkenes in the gas stream provided in (1) and contacted with a catalyst in (2) is in the range of from 5 to 100% by volume based on the total volume of the gas stream, preferably in the range of from 10 to 99 vol.-%, more preferably in the range of from 15 to 98 vol.-%, more preferably in the range of from 20 to 95 vol.-%, more preferably in the range of from 25 to 90 vol.-%, more preferably in the range of from 30 to 80 vol.-%, more preferably in the range of from 35 to 70 vol.-%, more preferably in the range of from 40 to 60 vol.-%, and more preferably in the range of from 45 to 55 vol.-%.

24. The process of any of embodiments 1 to 23, wherein the gas stream provided in (1) and contacted with a catalyst in (2) contains 50 vol.-% or less of aliphatic organic compounds based on the total volume of the gas stream, preferably 30 vol.-% or less, more preferably 20 vol.-% or less, more preferably 10 vol.-% or less, more preferably 5 vol.-% or less, more preferably 3 vol.-% or less, more preferably 2 vol.-% or less, more preferably 1 vol.-% or less, more preferably 0.5 vol.-% or less, more preferably 0.1 vol.-% or less, more preferably 0.05 vol.-% or less, more preferably 0.01 vol.-% or less, more preferably 0.005 vol.-% or less, and more preferably 0.001 vol.-% or less.

25. The process of embodiment 24, wherein the one or more aliphatic organic compounds are selected from the group consisting of optionally substituted and/or optionally cyclic and and/or optionally branched (C2-C20)hydrocarbons and mixtures of two or more thereof, preferably (C2-C16)hydrocarbons, more preferably (C2-C16)hydrocarbons, more preferably (C2-C14)hydrocarbons, more preferably (C2-C12)hydrocarbons, more preferably (C2-C10)hydrocarbons, more preferably (C2-C8)hydrocarbons, more preferably (C2-C6)hydrocarbons, more preferably (C3-C5)hydrocarbons, and more preferably C4-hydrocarbons and mixtures thereof.

26. The process of embodiment 25, wherein the one or more optionally substituted and/or optionally cyclic hydrocarbons are branched, wherein preferably the one or more branched hydrocarbons have the formula

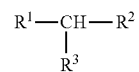

wherein independently from one another $R^1$, $R^2$, and $R^3$ are optionally substituted and/or optionally cyclic and/or optionally branched (C1-C8)alkyl, preferably (C1-C6) alkyl, more preferably (C1-C5)alkyl, wherein more preferably $R^1$, $R^2$, and $R^3$ are, independently from one another, optionally substituted and/or optionally branched (C1-C4)alkyl, preferably (C1-C3)alkyl, wherein more preferably $R^1$, $R^2$, and $R^3$ are, independently from one another, optionally substituted methyl or ethyl, preferably optionally substituted methyl.

27. The process of embodiment 25 or 26, wherein the one or more aliphatic organic compounds are substituted with one or more functional groups, wherein the one or more functional groups are preferably selected from the group consisting of hydroxyl, halogen, carbonyl, aldehyde, carbonate ester, carboxylate, carboxyl, ester, ether, carboxamide, amine, imine, cyanate, isocyanate, nitrate, nitrile, isonitrile, sulfide, sulfinyl, sulfonyl, sulfino, sulfo, thiocyanate, isothiocyanate, phosphino, phosphono, and phosphate,
more preferably from the group consisting of hydroxyl, halogen, carbonyl, aldehyde, carboxylate, carboxyl, ester, ether, carboxamide, amine, imine, cyanate, isocyanate, nitrate, nitrile, isonitrile, and combinations of two or more thereof,
more preferably from the group consisting of hydroxyl, halogen, carbonyl, aldehyde, carboxylate, carboxyl, ester, ether, and combinations of two or more thereof,
more preferably from the group consisting of hydroxyl, halogen, carbonyl, alkoxy, and combinations of two or more thereof,
more preferably from the group consisting of hydroxyl, fluoro, chloro, bromo, (C1-C3)alkoxy, and combinations of two or more thereof,
more preferably from the group consisting of hydroxyl, fluoro, chloro, (C1-C2)alkoxy, and combinations of two or more thereof,
more preferably from the group consisting of hydroxyl, fluoro, chloro, methoxy, and combinations of two or more thereof,
wherein more preferably the one or more aliphatic compounds are substituted with one or more hydroxyl groups.

28. The process of embodiment 25 or 26, wherein the one or more aliphatic organic compounds are unsubstituted hydrocarbons, wherein preferably the one or more aliphatic organic compounds comprise isobutane, wherein more preferably the one or more aliphatic organic compounds are isobutane.

29. The process of any of embodiments 1 to 28, wherein the gas stream provided in (1) and contacted with a catalyst in (2) further comprises one or more inert gases, wherein the one or more inert gases selected from the group consisting of nitrogen, helium, argon, $CO_2$, and mixtures of two or more thereof, preferably from the group consisting of nitrogen, argon, $CO_2$, and mixtures of two or more thereof, wherein more preferably the gas stream further comprises nitrogen and/or argon, more preferably nitrogen and argon.

30. The process of embodiment 29, wherein the content of the one or more inert gases in the gas stream provided in (1) and contacted with a catalyst in (2) is in the range of from 0 to 95% by volume based on the total volume of the gas stream, preferably in the range of from 1 to 90 vol.-%, more preferably in the range of from 2 to 85 vol.-%, more preferably in the range of from 5 to 80 vol.-%, more preferably in the range of from 10 to 75 vol.-%, more preferably in the range of from 20 to 70 vol.-%, more preferably in the range of from 30 to 65 vol.-%, more preferably in the range of from 40 to 60 vol.-%, and more preferably in the range of from 45 to 55 vol.-%.

31. The process of any of embodiments 1 to 30, wherein the contacting in (2) is conducted at a temperature in the range of from 80 to 350° C., more preferably of from 100 to 320° C., more preferably of from 120 to 300° C., more preferably of from 140 to 280° C., more preferably of from 160 to 260° C., more preferably of from 180 to 250° C., more preferably of from 200 to 245° C., more preferably of from 220 to 240° C., and more preferably of from 225 to 235° C.

32. The process of any of embodiments 1 to 31, wherein the contacting in (2) is conducted at a pressure in the range of from 2 to 80 bar, preferably of from 4 to 60 bar, more preferably of from 6 to 50 bar, more preferably of from 8 to 45 bar, more preferably of from 10 to 40 bar, more preferably of from 12 to 38 bar, more preferably of from 14 to 36 bar, more preferably of from 16 to 34 bar, more preferably of from 18 to 32 bar, more preferably of from 20 to 30 bar, more preferably of from 22 to 28 bar, and more preferably of from 24 to 26 bar.

33. The process of any of embodiments 1 to 32, wherein the contacting in (2) is conducted in a continuous mode and/or in a batch mode, preferably in a continuous mode.

34. The process of embodiment 33, wherein contacting in (2) is conducted in a continuous mode and wherein the space velocity in the contacting in (2) is in the range of from 10 to 10,000 $h^{-1}$, preferably of from 50 to 5,000 $h^{-1}$, more preferably of from 100 to 3,000 $h^{-1}$, more preferably of from 300 to 2,500 $h^{-1}$, more preferably of from 500 to 1,800 $h^{-1}$, more preferably of from 700 to 1,500 $h^{-1}$, more preferably of from 800 to 1,200 $h^{-1}$, more preferably of from 900 to 1,100 $h^{-1}$.

35. The process of embodiment 33 or 34, wherein contacting in (2) is conducted in a continuous mode and wherein the service life of the catalyst during which the continuous process is performed without interruption of the dimerization reaction is in the range of from 50 to 2,000 h, preferably from 100 to 1,000 h, more preferably of from 150 to 500 h, more preferably of from 200 to 400 h, more preferably of from 230 to 350 h, and more preferably of from 250 to 300 h.

36. The process of any of embodiments 1 to 35, wherein the process further comprises:
    (3) separating the unreacted one or more alkenes from the reacted mixture M1 obtained in (2) for obtaining a mixture M2 containing one or more alkenes; and
    (4) recycling the mixture M2 containing the one or more alkenes to (1).

37. The process of any of embodiments 1 to 36, wherein the catalyst is regenerated at regular intervals.

38. The process of embodiment 37, wherein regeneration is performed by contacting the catalyst with a gas stream containing oxygen, wherein contacting is performed at a temperature in the range of from 250 to 1,000° C., preferably of from 300 to 900° C., more preferably of from 350 to 800° C., more preferably of from 400 to 700° C., more preferably of from 450 to 650° C., and more preferably of from 500 to 600° C.

39. The process of embodiment 37 or 38, wherein the gas stream for regeneration contains oxygen in an amount of from 0.1 to 25% by volume based on the total volume of the gas stream, preferably of from 0.5 to 20 vol.-%, more preferably of from 1 to 15 vol.-%, more preferably of from 1.5 to 12 vol.-%, more preferably of from 2 to 10 vol.-%, more preferably of from 2.5 to 8 vol.-%, more preferably of from 3 to 7 vol.-%, more preferably of from 3.5 to 6 vol.-%, and more preferably of from 4 to 5 vol.-%.

40. The process of any of embodiments 37 to 39, wherein the gas stream for regeneration further comprises one or more inert gases, wherein the one or more inert gases selected from the group consisting of nitrogen, helium, argon, $CO_2$, and mixtures of two or more thereof, preferably from the group consisting of nitrogen, argon, $CO_2$, and mixtures of two or more thereof, wherein more preferably the gas stream further comprises nitrogen and/or argon, more preferably nitrogen and argon.

41. The process of any of embodiments 37 to 40, wherein the content of the one or more inert gases in the gas stream for regeneration is in the range of from 75 to 99.9% by volume based on the total volume of the gas stream, preferably in the range of from 80 to 99.5 vol.-%, more preferably in the range of from 85 to 99 vol.-%, more preferably in the range of from 88 to 98.5 vol.-%, more preferably in the range of from 90 to 98 vol.-%, more preferably in the range of from 92 to 97.5 vol.-%, more preferably in the range of from 93 to 97 vol.-%, more preferably in the range of from 94 to 96.5 vol.-%, and more preferably in the range of from 95 to 96 vol.-%.

42. The process of any of embodiments 1 to 41, wherein the zeolitic material having a BEA-type framework structure displays an X-ray diffraction pattern comprising at least the following reflections:

| Intensity (%) | Diffraction angle 2θ/° [Cu K(alpha 1)] |
|---|---|
| [12-32] | [21.79-21.99] |
| 100 | [22.28-22.48] |
| [8-28] | [25.18-25.38] |
| [19-39] | [25.71-25.91] |
| [6-26] | [26.96-27.16] |
| [5-25] | [28.62-28.82] |
| [5-25] | [29.43-29.63] |
| [4-24] | [30.23-30.43] |
| [4-24] | [33.06-33.47] |
| [4-24] | [43.21-43.61] | wherein 100% relates to the intensity of the maximum peak in the 20-45° 2θ range of the X-ray powder diffraction pattern, and wherein the BEA-type framework structure comprises $YO_2$ and $X_2O_3$, wherein Y is a tetravalent element, and X is a trivalent element.

43. The process of embodiment 42, wherein the zeolitic material having a BEA-type framework structure displays a $YO_2:X_2O_3$ molar ratio in the range of from 2 to 100, preferably from 3 to 50, more preferably from 4 to 30, more preferably from 5 to 25, more preferably from 6 to 20, more preferably from 7 to 18, more preferably from 8 to 16, and more preferably from 9 to 14.

44. The process of embodiment 42 or 43, wherein the zeolitic material comprises zeolite beta, wherein preferably the zeolitic material is zeolite beta.

45. The process of any of embodiments 1 to 44, wherein the zeolitic material having a BEA-type framework structure comprised in the catalyst is obtainable and/or obtained according to an organotemplate-free synthetic process.

46. The process of embodiment 45, the organotemplate-free synthetic process comprising
(A) preparing a mixture comprising one or more sources for $YO_2$, one or more sources for $X_2O_3$, and seed crystals, the seed crystals comprising a material having a BEA-type framework structure;
(B) crystallizing the mixture obtained in (A) for obtaining a zeolitic material having a BEA-type framework structure;
wherein Y is a tetravalent element, and X is a trivalent element, and
wherein the mixture prepared in (A) and crystallized in (B) does not contain an organotemplate as structure-directing agent.

47. The process of embodiment 46, wherein in the mixture prepared in (A) and crystallized in (B) contains 5 wt.-% or less of carbon calculated as the element and based on 100 wt.-% of Y contained in the mixture, preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, more preferably 0.001 wt.-% or less, more preferably 0.0005 wt.-% or less, and more preferably 0.0001 wt.-% or less of carbon calculated as the element and based on 100 wt.-% of Y contained in the mixture.

48. The process of embodiment 46 or 47, wherein the zeolitic material having a BEA-type framework structure obtained in (B) comprises one or more alkali metals AM, wherein AM is preferably selected from the group consisting of Li, Na, K, Cs, and combinations of two or more thereof, more preferably from the group consisting of Li, Na, K, and combinations of two or more thereof, wherein more preferably the alkali metal AM is Na and/or K, more preferably Na.

49. The process of embodiment 48, wherein the molar ratio $AM:YO_2$ in the mixture prepared in (A) and crystallized in (B) is in the range of from 0.05 to 5, preferably from 0.1 to 2, more preferably from 0.3 to 1, more preferably from 0.4 to 0.8, more preferably from 0.45 to 0.7, more preferably from 0.5 to 0.65, and more preferably from 0.55 to 0.6.

50. The process of any of embodiments 46 to 49, wherein Y is selected from the group consisting of Si, Sn, Ti, Zr, Ge, and a mixture of two or more thereof, Y preferably being Si.

51. The process of any of embodiments 46 to 50, wherein the one or more sources for $YO_2$ contained in the mixture prepared in (A) and crystallized in (B) comprises one or more silicates, preferably one or more alkali metal silicates, wherein the alkali metal is preferably selected from the group consisting of Li, Na, K, Rb, and Cs, wherein more preferably the alkali metal is Na and/or K, and wherein more preferably the alkali metal is Na, wherein more preferably the one or more sources for $YO_2$ contained in the mixture prepared in (A) and crystallized in (B) comprises water glass, preferably sodium and/or potassium silicate, more preferably sodium silicate.

52. The process of embodiment 51, wherein the one or more sources for $YO_2$ contained in the mixture prepared in (A) and crystallized in (B) further comprises one or more silicas, preferably one or more silica hydrosols and/or one or more colloidal silicas, and more preferably one or more colloidal silicas.

53. The process of any of embodiments 46 to 52, wherein X is selected from the group consisting of Al, B, In, Ga, and a mixture of two or more thereof, X preferably being Al.

54. The process of any of embodiments 46 to 53, wherein the one or more sources for $X_2O_3$ contained in the mixture prepared in (A) and crystallized in (B) comprises one or more aluminate salts, preferably an aluminate of an alkali metal, wherein the alkali metal is preferably selected from the group consisting of Li, Na, K, Rb, and Cs, wherein more preferably the alkali metal is Na and/or K, and wherein more preferably the alkali metal is Na.

55. The process of any of embodiments 46 to 54, wherein the molar ratio $YO_2:X_2O_3$ of the mixture prepared in (A) and crystallized in (B) is in the range of from 1 to 200, preferably from 5 to 100, more preferably from 10 to 50, more preferably from 15 to 40, more preferably from 20 to 30, more preferably from 23 to 25, and more preferably from 23.5 to 24.

56. The process of any of embodiments 46 to 55, wherein the amount of seed crystals comprised in the mixture prepared in (A) and crystallized in (B) is in the range of from 0.5 to 30 wt.-% based on 100 wt.-% of the one or more sources of $YO_2$ in the mixture, calculated as $YO_2$, preferably from 1 to 25 wt.-%, more preferably from 3 to 20 wt.-%, more preferably from 5 to 15 wt.-%, more preferably from 8 to 12 wt.-%, and more preferably from 9 to 11 wt.-%.

57. The process of any of embodiments 46 to 56, wherein the mixture prepared in (A) and crystallized in (B) further comprises one or more solvents, wherein said one or more solvents preferably comprises water, more preferably deionized water, wherein more preferably water is employed as the solvent further comprised in the mixture prepared in (A) and crystallized in (B), preferably deionized water.

58. The process of embodiment 57, wherein the molar ratio $H_2O:YO_2$ of the mixture prepared in (A) and crystallized in (B) is in the range of from 5 to 100, preferably from 10 to 50, more preferably from 13 to 30, more preferably from 15 to 20, and more preferably from 17 to 18.

59. The process of any of embodiments 46 to 58, wherein the crystallization in (B) involves heating of the mixture, preferably at a temperature in the range of from 80 to 200° C., more preferably from 90 to 180° C., more preferably from 100 to 160° C., more preferably from 110 to 140° C., and more preferably from 115 to 130° C.

60. The process of any of embodiments 46 to 59, wherein the crystallization in (B) is conducted under autogenous pressure, preferably under solvothermal conditions, and more preferably under hydrothermal conditions.

61. The process of embodiment 59 or 60, wherein in (B) the mixture is heated for a period in the range of from 5 to 200 h, preferably from 20 to 150 h, more preferably from 50 to 100 h, and more preferably from 65 to 75 h.

62. The process of any of embodiments 46 to 61, wherein the organotemplate-free synthetic process for the preparation of the zeolitic material having a BEA-type framework structure further comprises (C) isolating the zeolitic material having a BEA-type framework structure obtained in (B), preferably by filtration; and (D) optionally washing the zeolitic material having a BEA-type framework structure obtained in (B) or (C), preferably in (C); and/or, (E) optionally drying the zeolitic material having a BEA-type framework structure obtained in (B), (C) or (D), preferably in (D);

wherein the steps (C) and/or (D) and/or (E) can be conducted in any order, and wherein one or more of said steps is preferably repeated one or more times.

63. The process of embodiment 62, wherein the organotemplate-free synthetic process for the preparation of the zeolitic material having a BEA-type framework structure further comprises (F) exchanging one or more of the ionic non-framework elements contained in the zeolitic material having a BEA-type framework structure obtained in (C), (D), or (E), preferably in (E), against $H^+$ and/or $NH_4^+$, preferably against $NH_4^+$; and/or, preferably and (G) drying and/or calcining, preferably drying and calcining the zeolitic material having a BEA-type framework structure obtained in (C), (D), (E), or (F).

EXPERIMENTAL

Determination of the Acid Sites: Temperature Programmed Desorption of Ammonia (NH3-TPD)

The temperature-programmed desorption of ammonia ($NH_3$-TPD) was conducted in an automated chemisorption analysis unit (Micromeritics AutoChem II 2920) having a thermal conductivity detector. Continuous analysis of the desorbed species was accomplished using an online mass spectrometer (OmniStar QMG200 from Pfeiffer Vacuum). The sample (0.1 g) was introduced into a quartz tube and analysed using the program described below. The temperature was measured by means of a Ni/Cr/Ni thermocouple immediately above the sample in the quartz tube. For the analyses, He of purity 5.0 was used. Before any measurement, a blank sample was analysed for calibration.

1. Preparation: Commencement of recording; one measurement per second. Wait for 10 minutes at 25° C. and a He flow rate of 30 $cm^3$/min (room temperature (about 25° C.) and 1 atm); heat up to 600° C. at a heating rate of 20 K/min; hold for 10 minutes. Cool down under a He flow (30 $cm^3$/min) to 100° C. at a cooling rate of 20 K/min (furnace ramp temperature); Cool down under a He flow (30 $cm^3$/min) to 100° C. at a cooling rate of 3 K/min (sample ramp temperature).
2. Saturation with $NH_3$: Commencement of recording; one measurement per second. Change the gas flow to a mixture of 10% $NH_3$ in He (75 $cm^3$/min; 100° C. and 1 atm) at 100° C.; hold for 30 min.
3. Removal of the excess: Commencement of recording; one measurement per second. Change the gas flow to a He flow of 75 $cm^3$/min (100° C. and 1 atm) at 100° C.; hold for 60 min.
4. $NH_3$-TPD: Commencement of recording; one measurement per second. Heat up under a He flow (flow rate: 30 $cm^3$/min) to 600° C. at a heating rate of 10 K/min; hold for 30 min.
5. End of measurement.

Desorbed ammonia was measured by means of the online mass spectrometer, which demonstrated that the signal from the thermal conductivity detector was caused by desorbed ammonia. This involved utilizing the m/z=16 signal from ammonia in order to monitor the desorption of the ammonia. The amount of ammonia adsorbed (mmol/g of sample) was ascertained by means of the Micromeritics software through integration of the TPD signal with a horizontal baseline.

Reference Example 1: Synthesis Zeolite Beta (H-Form) from Organotemplate-Free Synthesis 12.693 kg of distilled water were provided in a 60 L autoclave. Two charges of 477.5 g of $NaAlO_2$ (commercially available from Aldrich) were each dissolved in 2.5 L of distilled water and added to the autoclave, wherein 3.5 L of distilled water were used for rinsing between the individual steps. 21.447 kg of sodium waterglass solution (26 wt.-% $SiO_2$ and 8 wt.-% $Na_2O$; commercially available from Woellner) were slowly added under stirring at 200 rpm, after which 3.762 kg of colloidal silica (Ludox® AS40 from Grace) were added and the resulting mixture stirred at 200 rpm for an additional 2 h. 717 g of zeolite Beta seeds (commercially available from Zeolyst International, Valley Forge, Pa. 19482, USA, under the tradename CP814C, which was converted to the H-form by calcination) were then added in smaller portions to the mixture, thus affording an aluminosilicate gel with a molar ratio of 1.00 $SiO_2$:0.042 $Al_2O_3$:0.29 $Na_2O$:17.49 $H_2O$. The reaction mixture was then crystallized in the autoclave under stirring at 100 rpm, wherein the mixture was heated in 3 h to 120° C. and held at that temperature for 67 h. The solid reaction product was then filtered off and washed to electroneutrality (conductivity of the wash-water <200 μS). The solid was dried over night at 120° C. in a drying oven for affording 1.9 kg of a white powder of zeolite beta displaying a crystallinity of 71% as determined from X-ray diffraction.

302 g of the zeolite beta obtained and 301 g of ammonium nitrate were then added to 2 kg of distilled water and stirred. The suspension was then transferred to a 4 L round bottom flask and the initial receptacle rinsed with 1 L of distilled water. The resulting mixture was then heated to 80° C. and kept at this temperature under continuous stirring for 2 h. The solid was filtered off and the filter cake was then dried for 3 h at 120° C. and then calcined at 450° C. for 5 h for affording 270 g of ion exchanged zeolite beta.

267 g of the zeolite beta product obtained from the first ion exchange step and 265.3 g of ammonium nitrate were then placed in a 5 L beaker and suspended in 2 kg of distilled water. The suspension was then transferred to a 4 L round bottom flask and the initial receptacle rinsed with 650 mL of distilled water. The resulting mixture was then heated to 80° C. and kept at this temperature under continuous stirring for 2 h. The solid was filtered off and the filter cake was then dried for 3 h at 120° C. and then calcined at 450° C. for 5 h for affording 234.2 g of ion exchanged zeolite beta.

233.4 g of the zeolite beta product obtained from the second ion exchange step and 233 g of ammonium nitrate were then placed in a 5 L beaker and suspended in 1.8 kg of distilled water. The suspension was then transferred to a 4 L round bottom flask and the initial receptacle rinsed with 550 mL of distilled water. The resulting mixture was then heated to 80° C. and kept at this temperature under continuous stirring for 2 h. The solid was filtered off and the filter cake was then dried for 3 h at 120° C. and then calcined at 450° C. for 5 h for affording zeolite beta in its H-form.

Elemental analysis of the product afforded: 4.9 wt.-% Al, 0.05 wt.-% Na, and 34 wt.-% Si.

Reference Example 2: Synthesis of ZSM-5

In a 2 m³ reactor 79.61 kg of distilled water is first introduced. To the water, 411.15 kg of an aqueous tetrapropylammonium hydroxide solution (TPAOH; 40 wt.-%) was added under stirring (70 rpm). The suspension is let for stirring for another 10 min. 8.2 kg solid NaOH is added slowly in 2.5 kg portions under stirring and after each portion the system is allowed to mix for 5 minutes. Next, 29.25 kg aluminium triisopropoxide is added to the suspension and the system is stirred for another 1 h. At the end, 538.19 kg colloidal silica (Ludox AS-40) is added followed by additional 10 kg of distilled water. The synthesis mixture is stirred another 1 h at room temperature before the reactor is flushed with nitrogen gas and the pressure reduced to −900 mbar. Afterwards the reactor is heated to 170° C. in 11 h. The hydrothermal synthesis is run for 72 h at 170° C. under 70 rpm stirring. After crystallization the synthesis mixture is cooled down to 30° C. The suspension is transferred to a larger vessel where the pH of the suspension is adjusted to 7±0.5, by addition of a 10 wt.-% aqueous nitric acid solution. The pH adjusted suspension is let for stirring for another 30 min at 70 rpm. The zeolite is separated by filtration and the filter cake is washed with distilled water until a conductivity of the wash water <200 µS. The filter cake is then dried at 120° C. for 96 h. The dried material was calcined to 550° C. in air for 6 h for obtaining a calcined ZSM-5 zeolite with a BET surface area of 390 m²/g, and displaying a crystallinity as determined by X-ray diffraction of 94%.

250 kg distilled water is added to a 400 L reactor and 25 kg ammonium nitrate is added under stirring (150 rpm). The suspension is heated to 80° C., followed by the addition of 25 kg of the calcined zeolite. The mixture is stirred further for 1 h at 80° C. Afterwards the reaction mixture is cooled down and filtered off using a filter press and washed with water until a conductivity in the wash water <200 µS. The ion-exchange process is then repeated for obtaining an ammonium-exchanged ZSM-5. The filter cake obtained after the second ammonium ion-exchange process is dried for 10 h at 120° C. and calcined at 500° C. in air for 5 h heating rate 2 C/min) for obtaining ZSM-5 in the H-form.

According to the elemental analysis the resulting product had the following contents determined per 100 g substance of <0.1 g carbon, 1.6 g aluminum, <0.01 g of sodium, and 43 g silicon.

The BET surface area was determined to be 408 m².

Reference Example 3: Determination of the Acid Sites

The acid sites and the total amount thereof was determined by temperature programmed desorption of ammonia for the zeolitic materials from Reference Examples 1 and 2 as well as for mordenite (CBV 21A, commercially available from Zeolyst), and zeolite beta (CP 814 E, commercially available from Zeolyst). The results are displayed in Table 1 below. The desorption peaks can be classified as corresponding to weak acid sites (Temperature at peak maximum<200° C.), medium acid sites (Temperature at peak maximum 200-400° C.) and strong acid sites (Temperature at peak maximum>400° C.).

TABLE 1

Results from temperature programmed desorption of ammonia (NH3-TPD)

| Catalyst | acid site strength | temperature at peak maximum [° C.] | quantity [mmol/g] |
|---|---|---|---|
| zeolite beta (Ref. Ex. 1) | medium | 217.5 | 1.785 |
| | strong | 595.9 | 0.01 |
| | total | | 1.795 |
| ZSM-5 (Ref. Ex. 2) | medium | 222.2 | 0.504 |
| | strong | 435.2 | 0.502 |
| | total | | 1.006 |
| mordenite (CBV 21A*) | medium | 215.4 | 0.653 |
| | strong | 563.9 | 0.995 |
| | total | | 1.648 |
| zeolite beta (CP 814E*) | medium (lower) | 206.4 | 0.733 |
| | medium (upper) | 315.5 | 0.322 |
| | strong | 538.8 | 0.026 |
| | total | | 1.081 |

(*) calcined for 5 h at 500° C.

Example 3: Catalytic Testing

The catalysts from Reference Example 1, as well as further catalysts were tested in the dimerization of isobutene (50 vol.-% gas feed) at different temperatures and pressures. The gas hourly space velocity for all reactions was 1,000 h⁻¹, wherein prior to the reaction, the respective catalyst was activated in an inert gas stream (90 vol.-% $N_2$ and 10 vol.-% Ar) over night. The further catalysts tested were mordenite (CBV 21A, commercially available from Zeolyst), Y zeolite (CBV-600 and CBV-300, respectively commercially available from Zeolyst), and zeolite beta (OP 814 E, commercially available from Zeolyst). All of the further catalysts tested were respectively calcined for 5 h at 500° C. prior to testing for conversion of the commercially available ammonium forms into the respective H-form. The results from testing are shown in Tables 2 and 3 below, wherein the C8 alkenes detected among the products produced in the reaction were 1-octene, 2,4,4-trimethyl-1-pentene, and 2,4,4-trimethyl-2-pentene. The results in Table 1 show the averaged values for the selectivity of the reaction towards C8 alkenes, non-C8 alkanes and alkenes and aromatics for 19 h time on stream, with the exception of Reference Example 1 for which the average values for 20 h time on stream are shown.

TABLE 2

Results from catalyst testing in the dimerization of isobutene

| | | | selectivities[%] | | |
|---|---|---|---|---|---|
| Catalyst | reaction temp. | reaction pressure | C8 alkene | non-C8 alkanes and alkenes | aromatics |
| zeolite beta (Ref. Ex. 1) | 230° C. | 25 bar | 57.18 | 36.29 | 6.53 |
| ZSM-5 (Ref. Ex. 2) | 230° C. | 25 bar | 34.27 | 55.38 | 10.35 |
| mordenite (CBV 21A*) | 150° C. | 20 bar | 15.86 | 67.45 | 16.69 |

TABLE 2-continued

Results from catalyst testing in the dimerization of isobutene

| Catalyst | reaction temp. | reaction pressure | selectivities[%] | | |
|---|---|---|---|---|---|
| | | | C8 alkene | non-C8 alkanes and alkenes | aromatics |
| mordenite** (CBV 21A*) | 150° C. | 20 bar | 82.14 | 17.86 | 0 |
| Y zeolite (CBV-600*) | 230° C. | 25 bar | 64.84 | 28.75 | 6.41 |
| Y zeolite (CBV-300*) | 230° C. | 25 bar | 70.00 | 24.38 | 5.62 |
| zeolite beta (CP 814E*) | 270° C. | 20 bar | 49.17 | 47.36 | 3.48 |

(*) calcined for 5 h at 500° C.
(**) after regeneration of the catalyst at 550° C. in a gas stream (GHSV = 1,000 h$^{-1}$) containing 4.5 vol.-% oxygen, 85.5 vol.-% nitrogen, and 10 vol.-% argon The results in in Table 3 show the averaged values for the conversion rates as well as the deactivation rates of the catalysts for 19 h time on stream, with the exception of Reference Example 1 for which the average values for 20 h time on stream are again shown.

TABLE 3

Results from catalyst testing in the dimerization of isobutene

| Catalyst | reaction temp. | reaction pressure | conversion rate | deactivation rate |
|---|---|---|---|---|
| zeolite beta (Ref. Ex. 1) | 230° C. | 25 bar | 90.64% | 0.035%/h |
| ZSM-5 (Ref. Ex. 2) | 230° C. | 25 bar | 96.29% | 0.164%/h |
| mordenite (CBV 21A*) | 150° C. | 20 bar | 99.36% | 0.006%/h |
| mordenite** (CBV 21A*) | 150° C. | 20 bar | 32.67% | 0.869%/h |
| Y zeolite (CBV-600*) | 230° C. | 25 bar | 51.31% | 1.265%/h |
| Y zeolite (CBV-300*) | 230° C. | 25 bar | 77.65% | 0.482%/h |
| zeolite beta (CP 814E*) | 270° C. | 20 bar | 86.99% | 0.479%/h |

(*) calcined for 5 h at 500° C.
(**) after regeneration of the catalyst at 550° C. in a gas stream (GHSV = 1,000 h$^{-1}$) containing 4.5 vol.-% oxygen, 85.5 vol.-% nitrogen, and 10 vol.-% argon As may be taken from the results provided in Tables 1 and 2, it has surprisingly been found that a process for the dimerization of alkenes affording a high selectivity towards the dimerization products, and in particular towards highly branched dimerization products, may be provided by using specific zeolitic materials as the catalyst. Furthermore, it has unexpectedly been found that the use of zeolitic materials not only allows for a maintenance of the dimerization reaction with a high alkene conversion rate over extended reaction times, but furthermore that the zeolitic materials may be easily regenerated and provide a performance comparable to the fresh catalyst even after regeneration cycles.

The invention claimed is:
1. A process for the dimerization of alkenes comprising
   (1) providing a gas stream comprising one or more alkenes; and
   (2) contacting the gas stream provided in (1) with a catalyst for obtaining a mixture M1 comprising one or more dimerization products of the one or more alkenes, wherein the catalyst in (2) comprises a zeolitic material having a framework structure type selected from the group consisting of MOR, BEA, FER, MFI, TON, FAU, and mixtures of two or more thereof,
   wherein the framework structure of the zeolitic material comprises $YO_2$, wherein Y stands for one or more tetravalent elements,
   wherein the zeolitic material comprised in the catalyst has a total amount of acid sites in a range of from 1.2 to 2.6 mmol/g; wherein the total amount of acid sites is defined as the total molar amount of desorbed ammonia per mass of the zeolitic material determined according to the temperature programmed desorption of ammonia (NH3-TPD).

2. The process of claim 1, wherein Y stands for one or more tetravalent elements, and wherein Y is selected from the group consisting of Si, Sn, Ti, Zr, Ge, and mixtures of two or more thereof.

3. The process of claim 1, wherein framework structure of the zeolitic material further comprises $X_2O_3$, wherein X stands for one or more trivalent elements, and wherein X is selected from the group consisting of Al, B, In, Ga, and mixtures of two or more thereof.

4. The process of claim 1, wherein the one or more alkenes provided in (1) comprise one or more alkenes according to formula (I)

wherein R and R' are alkyl groups.

5. The process of claim 1, wherein the one or more dimerization products of the one or more alkenes obtained in (2) comprise one or more alkenes according to formula (II)

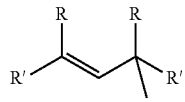

wherein R and R' are alkyl groups.

6. The process of claim 4, wherein independently from one another, R and R' are an optionally branched and/or optionally substituted and/or optionally unsaturated alkyl group selected from the group consisting of optionally branched and/or optionally substituted and/or optionally unsaturated C1-C6 alkyl groups.

7. The process of claim 1, wherein the gas stream provided in (1) and contacted with a catalyst in (2) contains 50 vol.-% or less of alkane or isobutane based on the total volume of the gas stream.

8. The process of claim 1, wherein the contacting in (2) is conducted at a temperature in the range of from 80 to 350° C.

9. The process of claim 1, wherein the contacting in (2) is conducted at a pressure in the range of from 2 to 80 bar.

10. The process of claim 1, wherein the contacting in (2) is conducted in a continuous mode or in a batch mode.

11. The process of claim 1, wherein the process further comprises:
    (3) separating the unreacted one or more alkenes from the reacted mixture M1 obtained in (2) for obtaining a mixture M2 containing one or more alkenes; and (4) recycling the mixture M2 containing the one or more alkenes to (1).

12. The process of claim 1, wherein the catalyst is regenerated at regular intervals.

13. The process of claim 1, wherein the zeolitic material having a BEA-type framework structure displays an X-ray diffraction pattern comprising at least the following reflections:

| Intensity (%) | Diffraction angle 2θ/° [Cu K(alpha 1)] |
| --- | --- |
| [12-32] | [21.79-21.99] |
| 100 | [22.28-22.48] |
| [8-28] | [25.18-25.38] |
| [19-39] | [25.71-25.91] |
| [6-26] | [26.96-27.16] |
| [5-25] | [28.62-28.82] |
| [5-25] | [29.43-29.63] |
| [4-24] | [30.23-30.43] |
| [4-24] | [33.06-33.47] |
| [4-24] | [43.21-43.61] | wherein 100% relates to the intensity of the maximum peak in the 20-45° 2θ range of the X-ray powder diffraction pattern, and wherein the BEA-type framework structure comprises $YO_2$ and $X_2O_3$, wherein Y is a tetravalent element, and X is a trivalent element.

14. The process of claim 1, wherein the zeolitic material having a BEA-type framework structure comprised in the catalyst is obtained by an organotemplate-free synthetic process, wherein the process does not contain an organotemplate as structure-directing agent.

* * * * *